US008005184B2

(12) United States Patent  
Chen

(10) Patent No.: US 8,005,184 B2  
(45) Date of Patent: Aug. 23, 2011

(54) ULTRA LOW RADIATION DOSE X-RAY CT SCANNER

(75) Inventor: Guang-Hong Chen, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 401 days.

(21) Appl. No.: 11/739,458

(22) Filed: Apr. 24, 2007

(65) Prior Publication Data

US 2008/0267484 A1     Oct. 30, 2008

(51) Int. Cl.  
A61B 6/03 (2006.01)
(52) U.S. Cl. .............................. 378/4; 378/21; 382/131
(58) Field of Classification Search .............. 378/4, 11, 378/21–26; 382/128, 131  
See application file for complete search history.

(56) References Cited

U.S. PATENT DOCUMENTS 5,909,476 A   6/1999   Cheng et al.

OTHER PUBLICATIONS

Bleuet et al., Resolution Improvement in Linear Tomosynthesis with an Adapted 3D Regularization Scheme, 2002, SPIE, vol. 4682, pp. 117-125).*
Zhu et al., Shift-invariant cone-beam FBP reconstruction on not less than a short scan, Aug. 2006, World Congress on Medical Physics and Biomedical Engineering 2006, p. 1002.*
Zeng et al., A Rotating and Warping Projector/Backprojector for Fan-beam and Cone-Beam Iterative Algorithm, 1994, IEEE Transactions on Nuclear Science, vol. 41, No. 6, pp. 2807-2811.*
Velikina et al., Limited view angle tomographic image reconstruction via total variation minimization, Feb. 18, 2007, SPIE Medical Imaging 2007: Physics of Medical Imaging, pp. 651020-1-651020-12.*
Nett et al., Planar tomosynthesis reconstruction in a parallel-beam framework via virtual object reconstruction, Feb. 18, 2007, SPIE Medical Imaging 2007: Physics of Medical Imaging, pp. 651028-1-651028-12.*
Bleuet et al., An Adapted Fan volume Sampling Scheme for 3D Algebraic Reconstruction in Linear Tomosynthesis, 2001, IEEE Nuclear Science Symposium Conference Record, vol. 3, pp. 1720-1724.*
Edholm et al., Divergent X-ray projections may under certain conditions be treated as parallel projections, 1998, Computer Methods and Programs in Biomedicine, vol. 57, pp. 91-94.*
Digital Breast Tomosynthesis (DBT), Mercury Computer Systems, Inc., 2005, 2 pages.

(Continued)

Primary Examiner — Edward J Glick  
Assistant Examiner — John M Corbett  
(74) Attorney, Agent, or Firm — Quarles & Brady LLP

(57) ABSTRACT

A line scan cone beam CT imaging system irradiates an object with an x-ray cone beam for multiple views. A projection data set of the object is acquired at each view. Between views, the cone beam and detector array are translated along parallel lines in opposite directions. An image is generated by converting the cone beam projection data set of the real object into a parallel-beam projection data set corresponding to a virtual object and using a total variation minimization image reconstruction algorithm to reconstruct a virtual image of the virtual object. The reconstruction algorithm includes the constraint that the Fourier transform of the reconstructed virtual image matches the known Fourier coefficients in the set of converted parallel-beam projections of the virtual object. The reconstructed virtual image is then transformed into an image of the real object.

5 Claims, 6 Drawing Sheets

OTHER PUBLICATIONS

Guang-Hong Chen, A novel extension of the parallel-beam projection-slice theorem to divergent fan-beam and cone-beam projections, Med. Phys. 32 (3), Am. Assoc. Phys. Med. Mar. 2005, pp. 654-665.

Guang-Hong Chen, Development and evaluation of an exact fan-beam reconstruction algorithm using an equal weighting scheme via locally compensated filtered backprojection (LCFBP), Med. Phys. 33 (2), Feb. 2006, Am. Assoc. Phys. Med., pp. 475-481.

Guang-Hong Chen, A new data consistency condition for fan-beam projection data, Med. Phys. 32 (4), Apr. 2005, Am. Assoc. Phys. Med., pp. 961-967.

T.Chan et al, Recent Developments in Total Variation Image, Dec. 24, 2004, pp. 1-18.

Antonin Chambolle et al, Image recovery via total variation minimization and related problems, Numer. Math. (1997) 76: 167-188.

* cited by examiner

ULTRA LOW RADIATION DOSE X-RAY CT SCANNER

STATEMENT REGARDING FEDERALLY SPONSORED RESEARCH

This invention was made with United States government support awarded by the following agency: National Institute of Health, Grant numbers: CA109992 and EB001683. The United States Government has certain rights in this invention.

CROSS-REFERENCE TO RELATED APPLICATIONS

Background of the Invention

Breast cancer is the most common cancer among women today. According to recent statistics, all women in the U.S. have a baseline risk of developing breast cancer of approximately 11-12 percent over the course of their lifetime and between 30-40 percent of women who develop breast cancer die from it. At this time, there is no certain way to prevent breast cancer. The best strategy is to detect breast cancer early and treat it before the cancer metastasizes.

X-ray screening mammography has been the most effective method for early detection of breast cancer and clinical studies have shown that it reduces mortality by 30 to 50 percent. However, about 30 percent of breast cancers are missed in conventional x-ray screening mammography. One of the major reasons for these false-negative diagnoses is that a cancerous mass is often obscured by overlapping breast tissues, which are referred to as "structure noise". The structure noise makes it difficult to perceive and characterize small lesions. This is particularly true for radiologically dense breasts. To compound matters, the superimposed normal breast tissues may mimic a spiculated tumor in a mammogram, which will cause a false-positive callback. Clinical studies have also shown that about 20 percent of mammography callbacks, even by experienced radiologists, are caused by superimposed normal glandular tissues.

In x-ray screening mammography, the median size of detectable cancers is about 11 mm, which contains about $10^9$ neoplastic cells in a primary tumor. However, the metastasis may have occurred about 16 months before the tumor reaches a detectable size in mammography. A reduction in the median size of a detectable cancer from 11 mm to 3 mm can lead to an 18-month earlier detection of the breast cancer. Therefore, a crucial step on the pathway of the eradication of breast cancer is to develop an imaging modality to enable the early detection of breast cancer at the median size of 3 mm. For a much greater percentage of women, this will allow clinicians to detect and treat the breast cancer before it metastasizes.

In order to significantly improve the sensitivity and specificity of breast cancer detection, it is necessary to use an imaging modality with three-dimensional imaging capability. The known three-dimensional x-ray imaging modalities include conventional computed tomography (CT) systems, tomosynthesis imaging systems, and dedicated cone-beam CT breast imaging systems. Despite the fact that conventional x-ray CT has been found useful in detecting lesions and implants in the breast, it is not a suitable technique for breast cancer screening. This is primarily due to the fact that x-ray photons have to penetrate through non-breast tissues in a conventional CT scan, which leads to substantial dose inefficiency.

In order to achieve three-dimensional breast imaging using the same or lower radiation dose as two-view mammography (4mGy average glandular dose), dedicated tomosynthesis and cone-beam CT systems have been proposed and investigated by several groups. The system design for most tomosynthesis breast imaging systems is based on current x-ray mammography. In these systems, the patient is standing, and the breast is slightly compressed by two plastic plates. The x-ray detector is stationary and mounted under the breast while the x-ray source rocks around the breast in an arc trajectory. In contrast, the patients are in a prone position in dedicated breast cone-beam CT systems. The breast is pendant, and the x-ray source and detector rotate around the breast beneath the patient's chest.

Current research activities in cone-beam CT and tomosynthesis breast imaging focus on removing structure noise to improve cancer detection sensitivity and specificity. Between these two modalities, tomosynthesis imaging provides better in-plane spatial resolution (xy-resolution) but lower spatial resolution in the third dimension (z-resolution); while cone-beam CT may provide isotropic spatial resolution to better delineate the tumor shape. However, due to the limitations of the state of the art image reconstruction methods in limited view angle tomosynthesis, significant image blurring between different image planes still remains. Thus, a significant amount of structure noise remains in the reconstructed images. This results in inferior contrast resolution in tomosynthesis. In comparison, cone-beam CT offers superior contrast resolution which will potentially enable a clinician to distinguish a cancerous mass form the surrounding glandular breast tissue.

In conventional CT imaging systems, it is well known that a single view of parallel beam x-ray projection data corresponds to one radial line in Fourier space. If the number of detector elements is $N_D$, then the number of view angles to satisfy the Nyquist sampling requirement is $N_p = \pi N_D / 2$. This dictates that the angular sampling must be finer than $\Delta\theta = \pi / N_p = 2/N_D$. Suppose $N_D$ to be 256 for a 256×256 image, then the required number of projections is about 400 and the angular sampling distance should be smaller than $\Delta\theta = 2/256 = 1/128$. This sampling rate should be satisfied by any two adjacent projections. If projection data is acquired from a limited range of view angles, for example, [−60°, +60°], one third of the Fourier space will not be filled by any Fourier data. Moreover, if only 30 projections are acquired, the angular sampling rate is $\pi/45$, which is nine times sparser than the Nyquist sampling requirement of $\Delta\theta = 1/128$.

SUMMARY OF THE INVENTION

The present invention provides a line scan cone beam CT imaging system that provides both high in-plane spatial resolution and excellent low contrast detectability, thereby combining the advantages of tomosynthesis and conventional CT. Such a system is extremely advantageous for imaging breasts. In one embodiment, an x-ray cone beam irradiates an object and a two dimensional x-ray detector array is used to acquire multiple views of projection data at predefined view angles. Between views, the cone beam is moved along a translational axis in a plane at a constant perpendicular distance (z) form an imaging plane (xy) in the object, and the detector array is likewise moved in the opposite direction along a parallel translational axis located on the opposite side of the object.

Another aspect of the present invention is an image reconstruction method that enables an image to be produced from a limited range of view angles acquired using the oppositely directed translational motion of the x-ray source and detector. In one embodiment, a projection data set is acquired form a limited range of view angles, and within this limited range Fourier space is vastly undersampled, thereby limiting the radiation exposure of the object being imaged. For example, projection data from 10-30 views is obtained within a limited view angle range of −60 degrees to +60 degrees. An image is then generated by converting a cone beam projection data set of a real object into a parallel-beam projection data set corresponding to a virtual object and using a novel image reconstruction method. The image reconstruction method generates an initial image of the virtual object (initial reconstructed virtual image) and calculates a metric which measures image quality, such as total variation, wherein the values of pixels in the reconstructed virtual image are updated using that calculated metric. The updated virtual image is then transformed into Fourier space, and this Fourier space data is constrained by replacing certain values with the measured Fourier coefficients in the set of converted parallel-beam projections. The constrained Fourier space data is transformed into a constrained reconstructed virtual image, and the image quality metric is again calculated. The steps are repeated until the constrained virtual image meets a preset quality as determined by the calculated metric. The constructed virtual image can then be transformed into an image of the real object.

These particular objects and advantages may apply to only some embodiments falling within the claims and thus do not define the scope of the invention.

DETAILED DESCRIPTION OF THE PREFERRED EMBODIMENT

Figure 1:
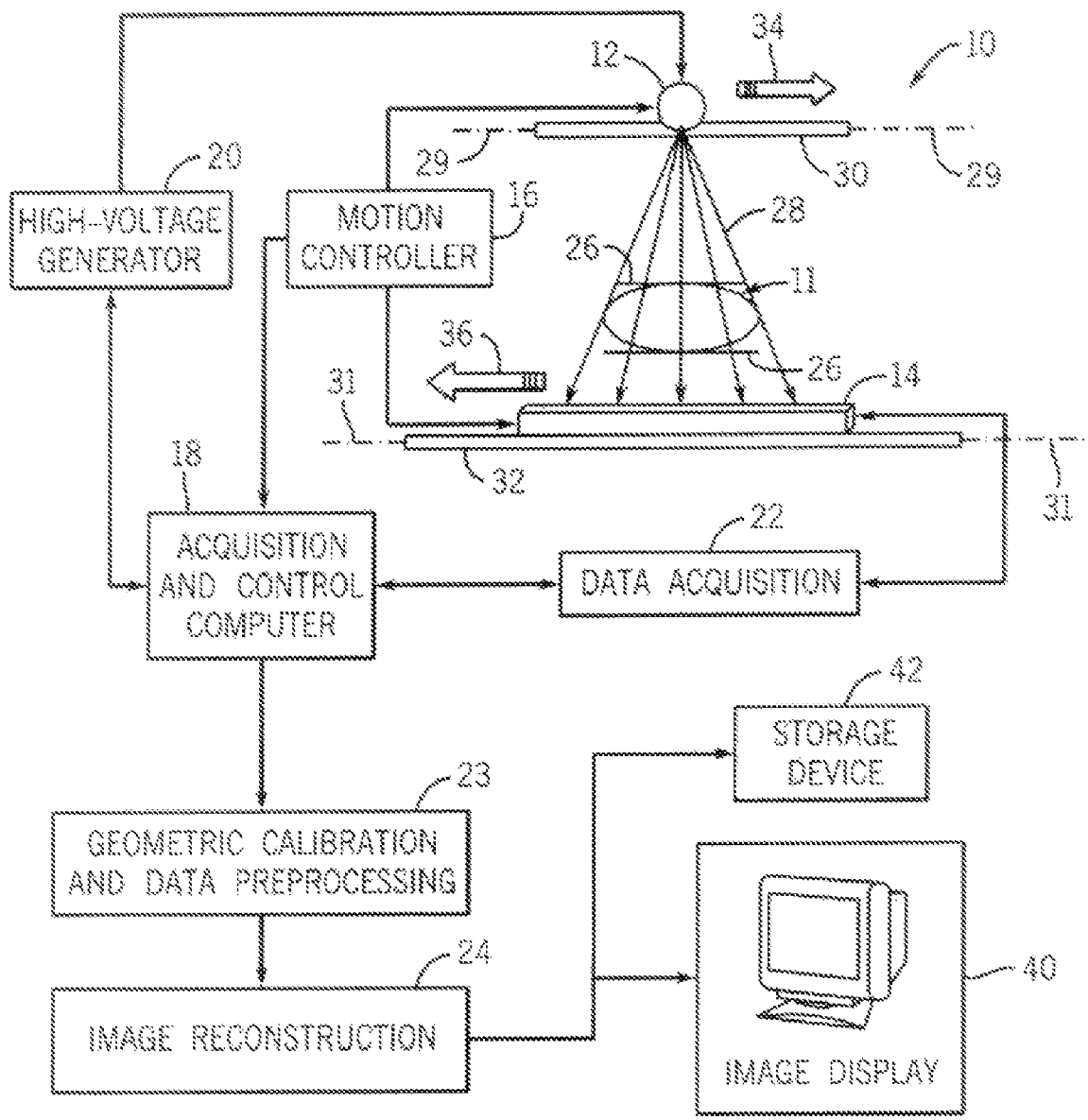
FIG. 1 is a schematic illustration of the line scan cone beam CT imaging system for imaging a breast.

FIG. 1 is a schematic illustration of the line scan cone beam CT imaging system 10 for generating an image of an object 11 such as a breast. CT imaging system 10 includes an x-ray source 12, a detector array 14, and a motion controller 16 to control the motion of the x-ray source 12 and the detector array 14, with the motion controller 16 under the direction of an acquisition and control computer 18. the acquisition and control computer 18 also controls a high voltage generator 20 for activating the x-ray source 12 as desired and further controls a data acquisition module 22. A geometric calibration and data preprocessing module 23 and an image reconstruction module 24 are also included to provide processing capabilities for the CT imaging system 10.

When used to image breasts, system 10 can be constructed as a table top system so that during an imaging procedure, similar to conventional x-ray mammography, a patient is standing and the breast is held by two plastic plates 26. Unlike conventional x-ray mammography, because multiple two-dimensional images of different slices can be produced by this system, the breast does not need to be highly compressed thereby eliminating much of the discomfort commonly associated with conventional mammography.

Similar to a conventional CT imaging system, a scan of a desired object such as a breast is performed using CT system 10 by acquiring projection view data at a plurality of view angles and reconstructing an image using the complete projection data set. However, the CT system 10 performs a line scan rather than a circular or spiral scan around the object. Further, by limiting the number of views in a scan, the CT system 10 exposes the object being imaged to low doses of radiation.

In particular, the x-ray source 12 supplies x-rays in a cone beam 28 to irradiate the object 11 being imaged. The x-ray cone beam 28 passes through the object 11 and impinges upon the detector array 14, which is preferably a flat panel, two-dimensional array of detector elements. The intensity of the transmitted radiation is dependent upon the detector array 14 produces a separate electrical signal that is a measurement of the beam attenuation. The attenuation measurements from all the detector elements are acquired separately to produce intensity data corresponding to one projection view at a particular view angle.

To acquire sufficient data to reconstruct an image, multiple projection views at different view angles are acquired. This is achieved by translating the x-ray source 12 and the detector array 14 along parallel axes in opposite directions in what is referred to herein as a "line scan". The x-ray source 12 moves along a track 30 disposed along a first translational axis 29 in one direction denoted by arrow 34, and the detector array 14 moves along a track 32 disposed along a second translational axis 31 in the opposite direction denoted by arrow 36. The translational axes 29 and 31 are parallel to each other and disposed on opposite sides of the object 11 being imaged. The translational axis 31 lies in the plane of the 2D detector array 14 and the path defined by the travel of the x-ray source 12 is parallel to the plane of the detector array 14. In order to obtain an image of the object in the x-y plane, the x-ray source 12 and the detector array 14 travel distances proportional to their respective distances from a system isocenter 304 as illustrated in FIG. 2(a).

Figure 2A:
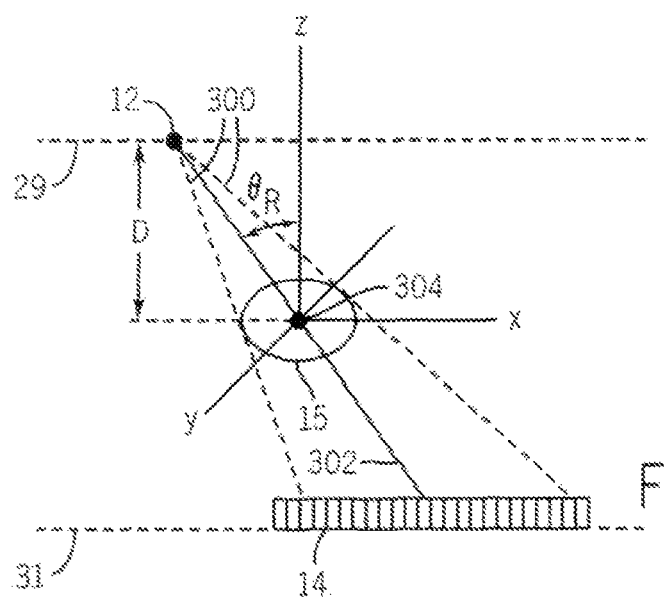
FIGS. 2(a)-2(c) are illustrations of different projection views using the CT imaging system of FIG. 1.
Figure 2B:
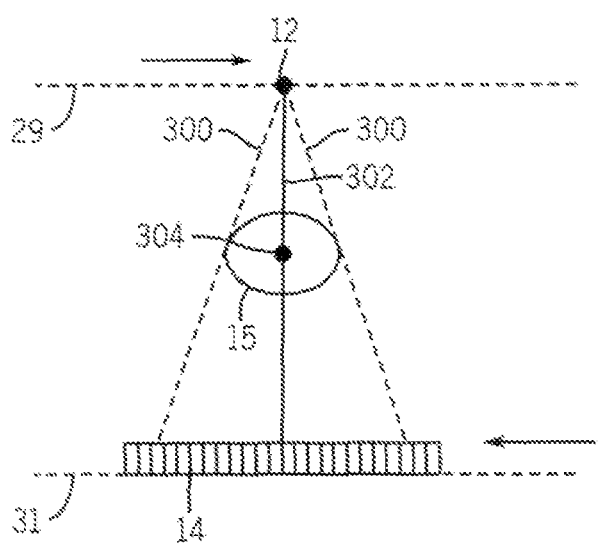
Figure 2C:
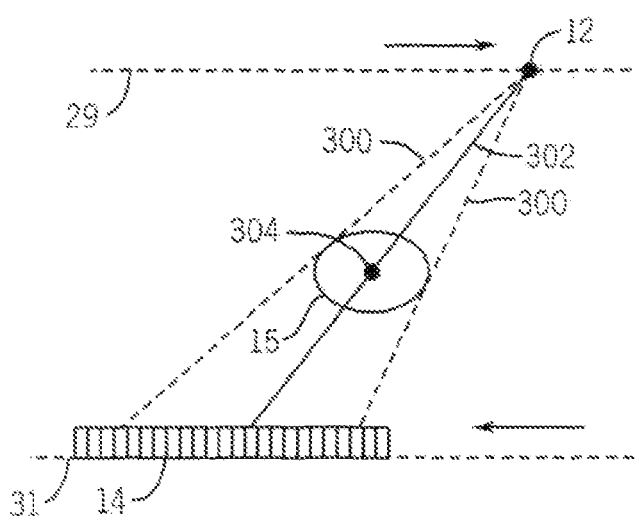

As shown in FIG. 2(a), when the x-ray source 12 is translated to its limit in one direction, the detector array 14 is translated to its limit in the opposite direction. A cone beam indicated by dashed lines 300 is directed toward the object 11 and the detector array 14. The isoray (center beam) indicated by line 302 of the cone beam passes through a system isocenter 304. System isocenter 304 is located at point (0, 0, 0) of the x y z coordinate system illustrated. As the scan is conducted, the x-ray source 12 and detector array 14 translate along respective axes 29 and 31 to a centered position as shown in FIG. 2(b), and then to the position shown in FIG. 2(c) in which they reach their opposite limits form those illustrated in FIG. 2(a). At all positions, or view angles, during this scan the isoray 302 is directed through the system isocenter 304. As shown in FIG. 2(a), each acquired projection view is characterized by its view angle $\theta_R$, which is the angle between a vertical line passing through the system isocenter 304 and the isoray 302.

The data acquisition module 22 is operable to sample analog intensity data from the detector elements of detector 14 and convert the data to digital signals for subsequent processing. Geometric calibration and data preprocessing is performed on these digital signals using mode 23 to generate a projection data set of the object which includes data from each of the acquired projection views. The image reconstruction module 24 operates on this acquired projection data set to perform a high speed image reconstruction and other processing according to the methods described herein to generate a reconstructed image. The reconstructed image can then be displayed on an image display device 40 and/or stored in a mass storage device 42.

Figure 3:
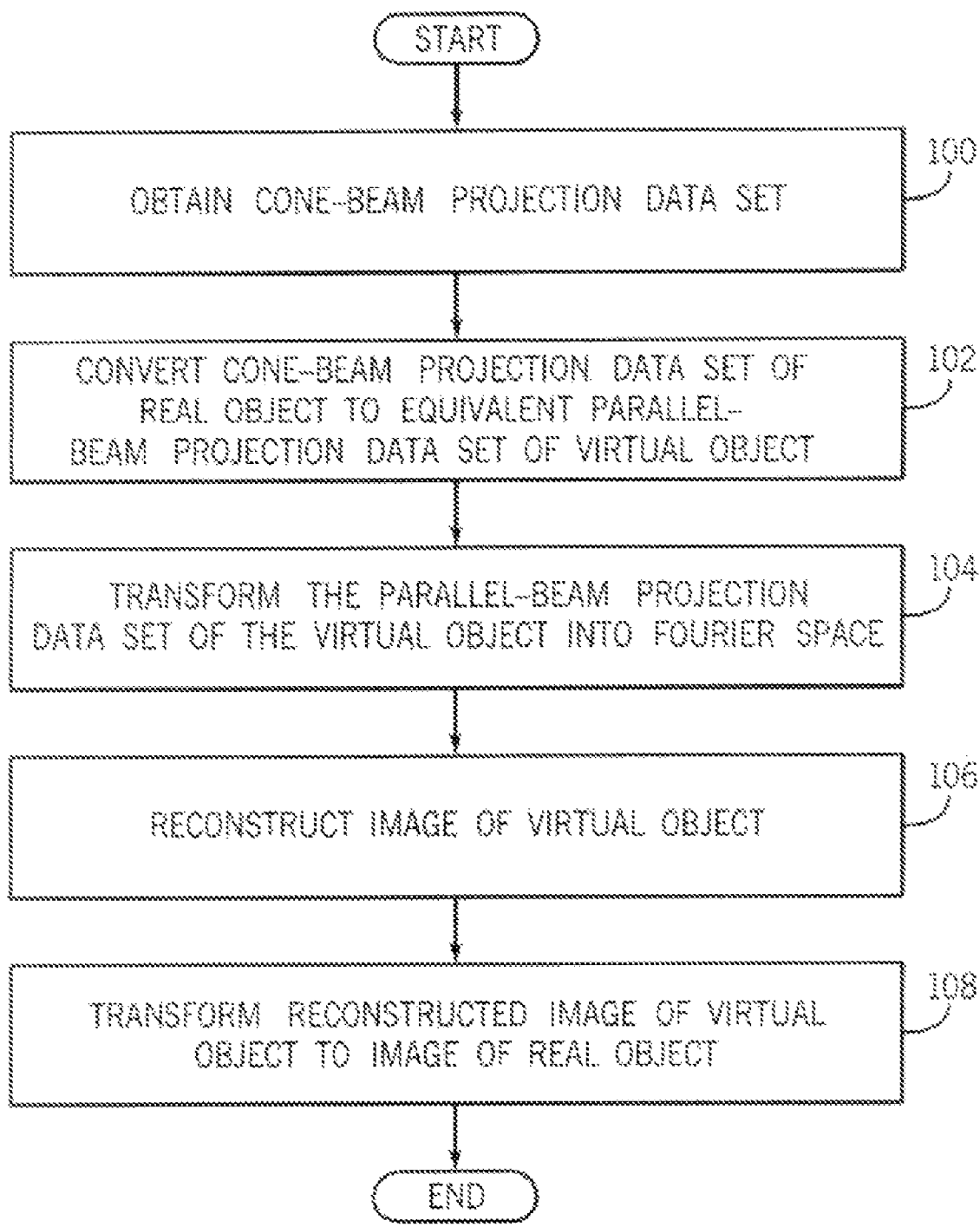
FIG. 3 is a flow chart of a method for generating an image of a real object according to the present invention.

FIG. 3 illustrates the steps performed by the imaging system 10 to produce an image of the object 11, which is referred to herein as a "real object". In particular, as indicated by process block 100, the image system 10 acquires a projection data set including data from multiple projection views of the real object. Each view is obtained at a different view angle $\theta_R$. For example, the projection data set includes data obtained from 10 to 30 views acquired over a view angle range −60 to +60 degrees. This is below the Nyquist sampling requirement.

Figure 4A:
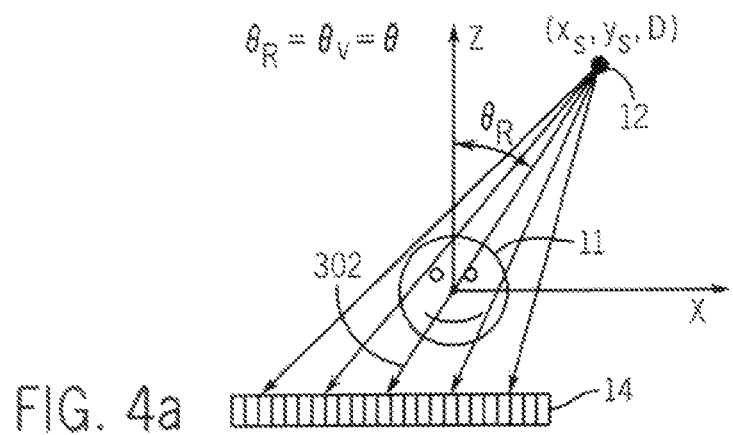
FIGS. 4(a)-(b) are pictorial views illustrating a conversion form a divergent-beam projection of a real object to a parallel-beam projection of a virtual object which forms part of the method of FIG. 2.
Figure 4B:
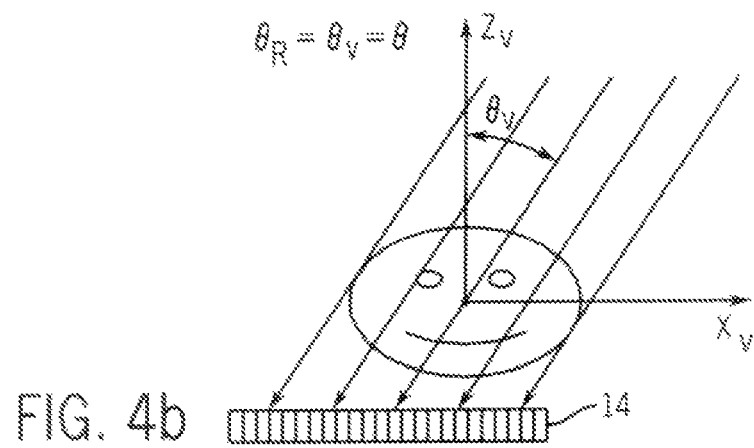

As indicated by process block 102, the cone beam projection data set of the real object is converted into a parallel beam projection data set associated with a virtual object. This is schematically illustrated in FIGS. 4(*a*) and 4(*b*) for a single view. As shown in FIG. 4(*a*), the x-ray source 12 is located at coordinates (x, y, D) of the xyz coordinate system for the illustrated view angle $\theta_R$ an data is acquired by detector 14. Then, for each detector element, its corresponding data value is converted into a corresponding parallel beam value associated with a virtual view angle θ, which is the same as view angle $\theta_R$, and denoted henceforth simply by θ. The conversion uses a preweighting factor which is individually determined for each detector element of the detector array 14.

Figure 7:
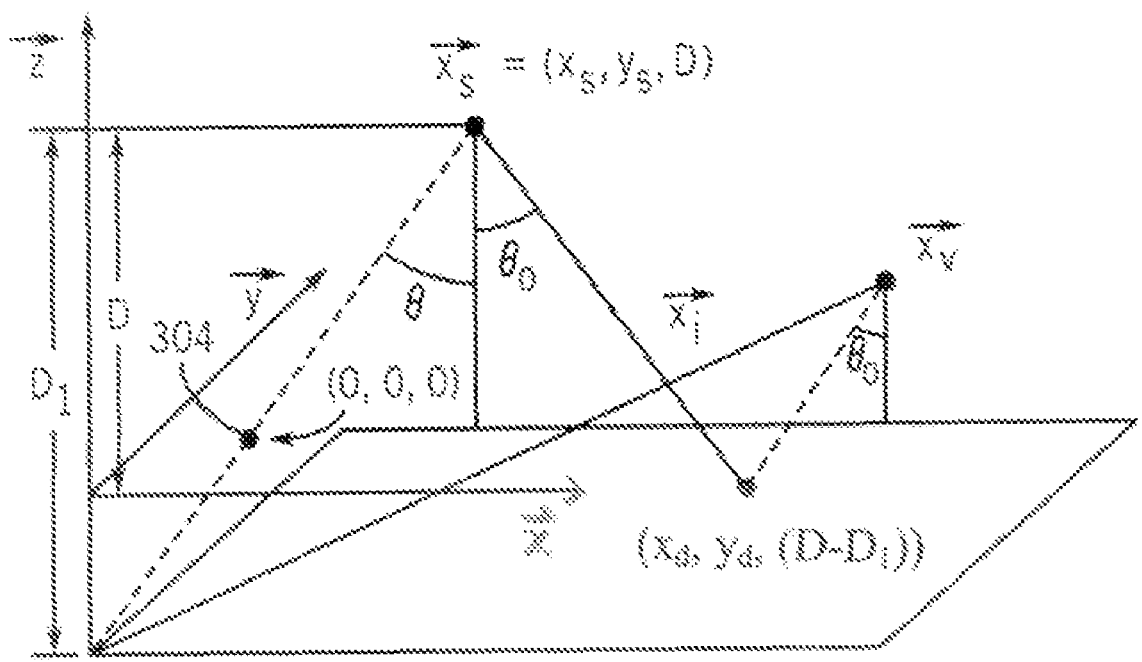
FIG. 7 is an illustration of locations of the x-ray source and detector array which aids to the understanding of the conversion of measured detector element values to those corresponding to a virtual object.

Specifically, referring to FIG. 7, for each view angle θ, a ray labeled by its angle $\theta_0$ is "converted" to a ray parallel to the isoray 302, and in this conversion, each detector element value is converted to a value equivalent to what would be detected by such a parallel ray. In this conversion, a value associated with the detector element of iso-ray 302 does not change, but all the other detector elements associated with other rays in the cone beam (or fan beam) are converted.

Thus, if a detector element located at coordinates (x, y, (D−D)) (using the xyz coordinates system illustrated in FIG. 2(*a*) wherein (x, y, D) are the coordinates of the x-ray source position and the system isocenter 304 is at (0, 0, 0)) and the detector element detects a value denoted by $P(\theta, \theta_0)$, then the same detector element is associated with a value denoted $P(\theta_0)$ for the virtual object according to the following:

$$P_v(\theta_0) = \frac{D}{D_1} \frac{\cos\theta_0}{\cos\theta} P(\theta, \theta_0) = \frac{\sqrt{x_s^2 + y_s^2 + D^2}}{\sqrt{(x_d - x_s)^2 + (y_d - y_s)^2 + D_1^2}} P(\theta, \theta_0) \qquad \text{Equation 1}$$

where:

$$\cos\theta = \frac{D}{\sqrt{x_s^2 + y_s^2 + D^2}} \qquad \text{Equation 2}$$

and $$\cos\theta_0 = \frac{D_1}{\sqrt{(x_d - x_s)^2 + (y_d - y_s)^2 + D_1^2}} \qquad \text{Equation 3}$$

In this manner, a complete parallel beam projection data set is formed.

Referring back to FIG. 3, as indicated at process block 104, the parallel beam projection data set associated with the virtual object is then transformed into Fourier space for each of the plurality of projection views. This is easily accomplished using the projection slice theorem. A set of known Fourier coefficients in Fourier space are obtained. These known Fourier coefficients are on a plurality of predetermined radial lines in Fourier space (k-space), with each radial line corresponding to one of the predetermined virtual view angles θ of the virtual projection data set.

As indicated at process block 106, an image of the virtual object is then reconstructed from this Fourier space data preferably using the method described in detail below with reference to FIG. 6.

As indicated at process block 108, the reconstructed image of the virtual object is then transformed to an image of the real object using a relationship between a virtual image point and a real image point. A real point at location (x, y, z) can be transformed into a virtual image point (x, y, z) using the following equations:

$$x_v = \frac{D_1}{D - z} x \qquad \text{Equation 4}$$

$$y_v = \frac{D_1}{D - z} y \qquad \text{Equation 5}$$

$$z_v = \frac{D_1}{D - z} z \qquad \text{Equation 6}$$

Here D denotes the z coordinate of the x-ray source position, and D denotes the distance form the x-ray source to the detector along the z axis, using the coordinate system illustrated in FIG. 2(*a*), wherein the point (0,0,0) is at the system isocenter 304. These equations define how a geometrical shape of the real image object will be deformed into a virtual object. For example, a circular image object will be converted into an oval shaped virtual object. A square shaped image object will be converted into a trapezoidal shaped image virtual object.

The image function f(x, y, z) is transformed into a virtual image function $F_v(x_v, y_v, z_v)$ by the following:

$$f_v(x_v, y_v, z_v) = \left(\frac{D-z}{D_1}\right)^2 f(x, y, z) \qquad \text{Equation 7}$$

$$f(x, y, z) = \left(\frac{D_1}{D-z}\right)^2 f_v(x_v, y_v, z_v) \qquad \text{Equation 8}$$

These two formulas give a nonsingular conversion between the image values of the virtual object and the actual image values of a real image object. An image of the real object can thus be calculated and can be displayed and stored as described above.

Figure 5:
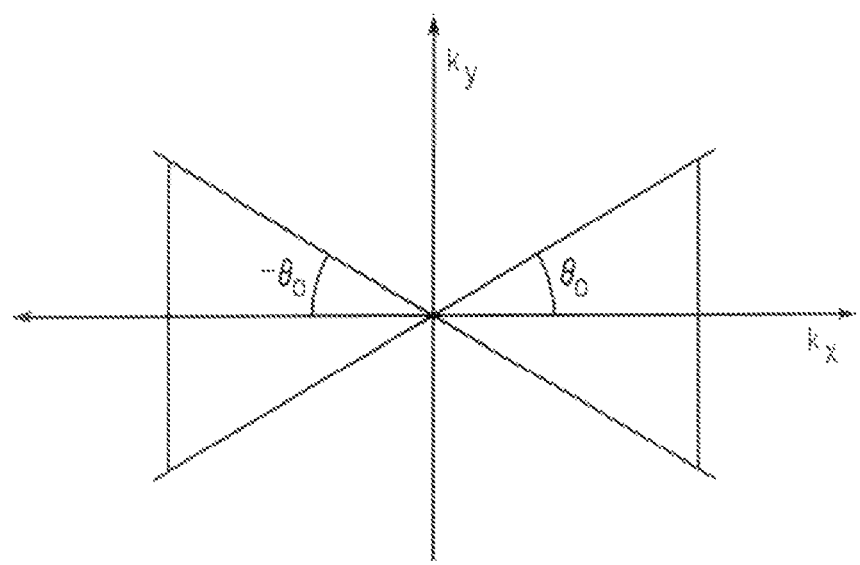
FIG. 5 is a Fourier space representation of the data acquired with parallel-beam projections acquired in an angular range of view angles ranging from +θ degrees to −θ degrees.

An important step in the above-described method is the reconstruction of an image from the limited set of Fourier space data acquired using the above-described CT system 10. According to the well-known Nyquist sampling theorem, 10-30 projections do not enable reconstruction of a streak-free image using well-known conventional reconstruction methods such as a filtered backprojection reconstruction techniques or a direct inverse Fourier transform reconstruction technique. When 10-30 projections are acquired over a limited range of view angles θ (e.g., −60 degrees to +60 degrees), there are two large regions in the Fourier space that are not sampled, as illustrated in FIG. 5. In this case, besides streak artifacts, severe image distortion artifacts are also typically present in the reconstructed image using conventional methods. However, reconstructing an image using the method according to the present invention reduces the number and extent of these artifacts.

Figure 6:
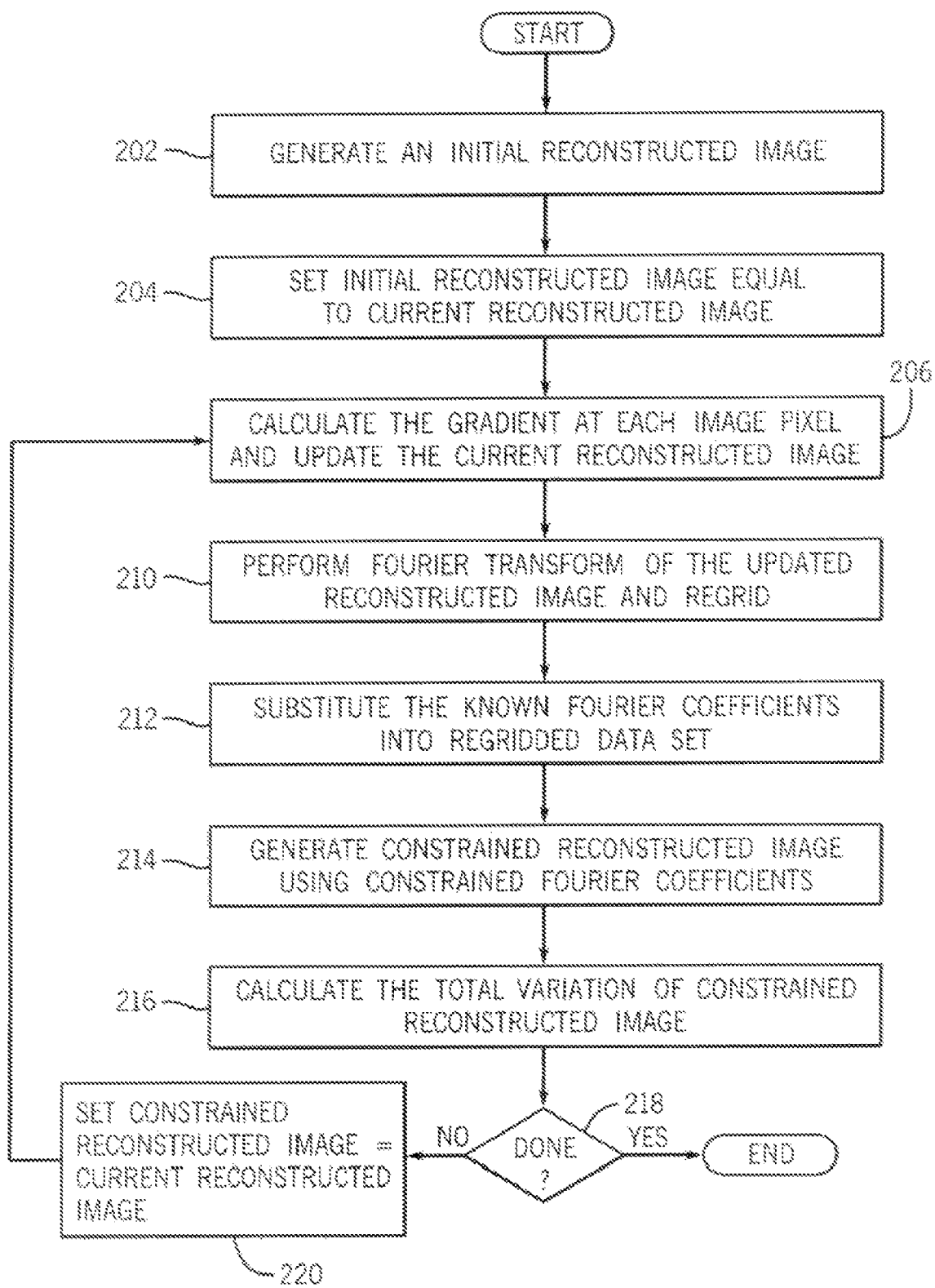
FIG. 6 is a flow chart illustrating the preferred method for reconstructing the virtual image using total variation minimization which forms part of the method of FIG. 2.

Referring particularly to FIG. 6, a method for using total variation minimization to reconstruct an image of the virtual object using the parallel projection data set corresponding to the virtual image will now be described in detail.

As indicated at process block 202, using the set of known Fourier coefficients corresponding to the virtual object, an initial reconstructed image (or seed image) is generated using for example any one of the well-known conventional reconstruction methods such as a filtered backprojection reconstruction technique or an inverse Fourier transform reconstruction technique. The initial reconstructed image includes a plurality of pixels with a respective image value associated with each pixel.

At process block 204, the initial reconstructed image is set as a current reconstructed image.

As indicated at process block 206, the current reconstructed image is then updated. This can be performed using a total variation steepest descent calculation at each image pixel. In particular, at each pixel, an image value variation is calculated and the total variation (TV) of an image, defined as a function of the image value variation at all the pixels, is defined as follows:

$$TV = \sum_{m,n} \sqrt{(f(m+1,n) - f(m,n))^2 + (f(m,n+1) - f(m,n))^2} \quad \text{Equation 9}$$

where the summation is conducted over all the image pixels labeled by the indices (m, n), where f(m, n) is the corresponding image pixel value at an image pixel (m, n). Total variation is one example of a metric which measures the quality of an image.

The pixels in the current reconstructed image can then be updated using the defined total variation. In particular, the gradient of the total variation (grad(TV)) is calculated at each pixel of the current reconstructed image and the image value of each pixel of the current reconstructed image is updated using the gradient at that pixel to generate an updated reconstructed image. This is a total variation steepest descent calculation. For example, each pixel value $f_k(m, n)$ is updated to produce a new pixel value $f_{k+1}(m, n)$ according to the following equation:

$$f_{k+1}(m, n) = f_k(m, n) - \alpha_x \text{grad}(TV)| \quad (10)$$

where α is a step length. For simplicity, the step length α may be set as a constant.

Each pixel value may be updated using the steps described in the previous paragraph several times. In one embodiment, these steps will be repeated L times, where L is a preset constant such as 20.

As indicated at process block 210, a Fourier transform of the updated reconstructed image is then performed to return to Fourier space. The results of the Fourier transform are regridded in Fourier space into radial lines which include the predetermined radial lines at the predetermined view angles θ to produce a set of updated Fourier coefficients.

As indicated at process block 212, those updated Fourier coefficients in the set which are on the predetermined radial lines are replaced with the corresponding known Fourier coefficients to thus generate a set of constrained Fourier coefficients.

As indicated at process block 214, a conventional reconstruction method such as a filtered backprojection reconstruction technique or an inverse Fourier transform reconstruction technique is performed using the set of constrained Fourier coefficients to generate a constrained reconstructed image of the object. Other reconstruction methods such as methods which perform fast Fourier transforms on a non-Cartesian grid can also be utilized.

At indicated at process block 216, the total variation of the constrained reconstructed image is calculated, using Equation 9 above.

At process block 218, it is determined whether the total variation of the constrained reconstructed image is below a predetermined value. In each pass, the total variation of the constrained reconstructed image should be smaller than a total variation of a prior reconstructed image, and once the calculated total variation of the constrained reconstructed image is below a predetermined value, this means that an image quality is meets a predefined quality metric, i.e., the image quality is satisfactory.

If the total variation is not below the predetermined value, at process block 220, the constrained reconstructed image is set as the current reconstructed image, and process blocks 206 to 216 are repeated until the total variation of the constrained reconstructed image is below the predetermined value.

Once the total variation is below the predetermined value, the process is complete, and the latest constrained reconstructed image of the virtual object can then be transformed into the real object, as described above.

It is specifically intended that the present invention not be limited to the embodiments and illustrations contained herein, but include modified forms of those embodiments including portions of the embodiments and combinations of elements of different embodiments as come within the scope of the following claims.

What is claimed is:

1. A line scan cone beam computed tomography (CT) system for generating an image of an object, the system comprising:

an x-ray source mounted for translational motion along a first axis and being operable to emit x-rays in a cone beam for irradiating the object at each of a plurality of view angles;

a detector array mounted for translational motion along a second axis and including a plurality of detector elements for measuring the intensity of the cone beam radiation transmitted through the object at each of the plurality of view angles;

a controller for controlling movement of both the x-ray source and the detector array to successive view angles, wherein movement of the x-ray source along the first axis occurs in a direction opposite the movement of the detector array along the second axis;

a data acquisition module that receives intensity measurements from the detector array corresponding to each of the plurality of view angles and produces digital signals indicative of the intensity measurements;

a processor that receives the digital signals, generates a cone beam projection data set of the object therefrom, and reconstructs the image of the object using the cone beam projection data set; and wherein the processor operates to:
i) convert the cone beam projection data set of the object into an equivalent parallel beam projection data set of a virtual object;
ii) transform the parallel beam projection data set to a corresponding set of known Fourier space data;

iii) reconstruct an initial image of the virtual object from the known Fourier space data set, the initial image having a plurality of pixels with associated values;
iv) update the values of the pixels in the reconstructed virtual image, using a defined metric which measures the quality of the reconstructed image, in order to produce an updated image;
v) transform the updated image to Fourier space to form an updated image Fourier space data set;
vi) replace Fourier space data in the updated image Fourier space data set with corresponding known Fourier space data to form a constrained Fourier space data set;
vii) reconstruct a constrained image of the virtual object from the constrained Fourier space data set;
viii) repeat operations iv) through viii) until the constrained image of the virtual object meets a preset quality as determined by calculating the defined metric of the constrained reconstructed image; and
ix) transform the constrained reconstructed image of the virtual object to an image of the object.

2. The system of claim 1, further including at least one of a storage device for storing the reconstructed image of the object and a display device for displaying the reconstructed image of the object.

3. The system of claim 1, wherein movement of the x-ray source and the detector array is controlled such that each travels a distance proportional to a respective distance from a system isocenter.

4. A method for reconstructing an image of an object from a set of projection data acquired at a plurality of view angles that do not meet the Nyquist sampling requirement, the steps comprising:
a) transforming the set of projection data to a corresponding set of known Fourier space data;
b) reconstructing an initial image from the known Fourier space data set;
c) defining a metric which measures the quality of the reconstructed image;
d) updating the values of pixels in the reconstructed image using the defined metric;
e) transforming the updated image to Fourier space to form an updated image Fourier space data set;
f) replacing some Fourier space data in the updated image Fourier space data set with the corresponding known Fourier space data to form a constrained Fourier space data set;
g) reconstructing a constrained image of the object from the constrained Fourier space data set; and
i) calculating the defined metric for the constrained reconstructed image, and
j) repeating steps c) through i) until the constrained image of the object meets a preset quality as determined by a metric calculated in step i).

5. A method for producing an image of a real object, the steps comprising:
a) acquiring x-ray cone beam projection view data of the real object at each of a plurality of different view angles using an x-ray source mounted for translational motion along a first axis and a detector array mounted for translational motion along a second axis;
b) converting the cone beam projection data of the real object into parallel beam projection data of a virtual object at each view angle to form a parallel beam projection data set;
c) transforming the parallel beam projection data set to a corresponding set of known Fourier space data,
d) reconstructing an initial virtual image having respective values corresponding to each of a plurality of pixels from the known Fourier space data set;
e) defining a total variation of the reconstructed virtual image;
f) calculated an updated value of each pixel in the reconstructed virtual image using a gradient of the total variation at that pixel to produce an updated virtual image;
g) transforming the updated virtual image to Fourier space to form an updated image Fourier space data set;
h) replacing a portion of the updated image Fourier space data set with corresponding known Fourier space data to form a constrained Fourier space data set;
i) reconstructing a constrained image of the virtual object from the constrained Fourier space data set; and
j) repeating steps e) through i) until a calculated total variation of the constrained image is below a predetermined threshold, then transforming the constrained image of the virtual object to an image of the real object using a relationship between a virtual image point and a real image point.

* * * * *